United States Patent

Suzuki et al.

[11] Patent Number: 5,287,191
[45] Date of Patent: Feb. 15, 1994

[54] CABLE CONNECTOR FOR SEPARABLE TYPE CAMERA HEAD

[75] Inventors: Takahisa Suzuki; Tatsuki Tsukada, both of Yokohama, Japan

[73] Assignee: Matsushita Electric Industrial Co., Ltd., Osaka, Japan

[21] Appl. No.: 879,903

[22] Filed: May 8, 1992

[30] Foreign Application Priority Data

May 20, 1991 [JP] Japan .................. 3-114767

[51] Int. Cl.$^5$ .................. H04N 5/30; H04N 5/225
[52] U.S. Cl. .................. 348/375; 348/373; 348/65
[58] Field of Search .................. 439/321, 333, 352; 358/209, 225, 229, 213.11, 98; H04N 5/225

[56] References Cited

U.S. PATENT DOCUMENTS

| | | | |
|---|---|---|---|
| 2,890,434 | 6/1959 | Ray et al. | 439/321 |
| 4,810,210 | 3/1989 | Komatsu | 439/610 |
| 4,838,805 | 6/1989 | Sturges | 439/321 |
| 4,918,521 | 4/1990 | Yabe et al. | 358/98 |
| 4,974,075 | 11/1990 | Nakajima | 358/98 |

FOREIGN PATENT DOCUMENTS

| | | | |
|---|---|---|---|
| 0080930 | 6/1983 | European Pat. Off. | H01R 13/621 |
| 2274181 | 1/1976 | France | H04N 5/26 |
| 61-59974 | 3/1986 | Japan | H04N 5/225 |

*Primary Examiner*—Joseph Mancuso
*Assistant Examiner*—Tuan V. Ho
*Attorney, Agent, or Firm*—Stevens, Davis, Miller & Mosher

[57] ABSTRACT

A separable camera head capable of attaching and detaching a camera cable by a connector system, wherein the camera head has an external appearance of a direct fitting cable structure. Lead terminal pins of an image sensing device module including image sensing devices, driving circuits and a spatial filter are inserted into a connector of a connector module having a cable clamp, a connector, a cable and a body chassis. Thereafter, a sheath chassis and the body chassis are united by a screw and a screw thread.

1 Claim, 3 Drawing Sheets

CABLE CONNECTOR FOR SEPARABLE TYPE CAMERA HEAD

BACKGROUND OF THE INVENTION

The present invention relates generally to a cable connecting structure of a solid state image sensing apparatus and, more particularly, to a camera cable connecting structure in a separate type camera composed of a camera head and a camera control unit.

In recent years, there has been a remarkably increasing demand for a separate type camera utilizing such a characteristic that a solid state image sensing device is easily reduced both in size and in weight. Under such circumstances, there has arisen a customer's new demand for a camera cable connecting method for connecting a camera head to a camera control unit (hereinafter abbreviated CCU), and especially a connecting mode for a camera head and a camera cable. Namely, a cable direct fitting type is desirable in terms of design as an external appearance of a connecting portion between the camera head and the camera cable. In terms of attaching and detaching the camera cable, however, it is desirable to incorporate a connector function.

The following is an explanation of a conventional method of connecting the camera head to the camera cable.

FIG. 1 illustrates a conventional cable direct fitting type connecting method. Designated at 31 in FIG. 1 is an image sensing device module unit having its lead terminals 35 to which terminal members 36 of a camera cable 34 are soldered. Thereafter, the image sensing device module unit is inserted into a body chassis 32 and a sheath chassis 33, and the connecting portion is fastened with a screw 37, whereby they are united. A cable direct fitting type camera head is thus completed. Note that a thread 38 is formed in an outer periphery of the sheath chassis 33; and a lens (not illustrated) is thereby mountable thereto.

FIG. 2 is another conventional example, showing a connector connecting method. FIG. 3 is a view fully illustrating a method of assembling the camera head. Referring to FIGS. 2 and 3, the numeral 51 represents an image sensing device module unit having its lead terminals (not shown) to which a connecting plate 52 made of a flexible material is soldered. Indicated at 53 is a connector constituting the other end (opposite to the lens mounting side) of the camera head and having its one end provided with the lead terminals soldered to the connecting plate and the other end provided with a male connector connected to a female connector 41 integrally soldered to the camera cable 42. The numeral 54 denotes a sheath chassis into which a unit 55 consisting of the image sensing device, the connecting plate and the male connector is inserted. These components are fastened with a screw 56, and then the body chassis 57 and the sheath chassis 54 are also fastened with a screw, thus completing the camera head 43. The customer uses the camera by connecting the male connector of the camera head to the female connector 41 of a cable assembly 44.

In the conventional example described above, however, the external appearance of the camera based on the construction of FIG. 1 satisfies the demand of the customer because of the cable direct fitting type. Attaching and detaching the camera cable, however, involve demounting and mounting by hyperfine soldering. This presents such a problem that the operation is not easy, and the customer's demand can not be satisfied. Further, in the construction of FIG. 2, the camera cable is attached and detached by the connector system, which facilitates the operation and meets the customer's demand. In terms of the external appearance of the camera, however, the size of the female connector 41 is substantially equal to that of the camera head 43, which lacks in style. Thus, a problem also arises, wherein the demand of the customer can not be satisfied.

SUMMARY OF THE INVENTION

It is an object of the present invention, which obviates the problem given above, to provide a solid state image sensing apparatus wherein a camera head takes a camera cable direct fitting type in its external appearance, and attaching and detaching of the camera cable are facilitated based on a connector structure incorporated into a camera.

To accomplish the object described above, in the solid state image sensing apparatus of the present invention, a special female connector unit to which a camera cable is soldered is connected to an image sensing device module having lead terminals and incorporating a pin function of a male connector. Thereafter, a sheath chassis of the image sensing device module is united with a body chassis incorporating a female connector unit by screw-fastening, thus constructing a camera head.

Hence, according to the construction of the present invention, in the camera head, the female connector unit with the camera cable is connector-fitted to the sheath chassis member incorporating the image sensing device module with pin lead terminals. Next, the connector unit is covered with the body chassis, and the body chassis and the sheath chassis are united by screw-fastening. Therefore, the camera head takes the cable direct fitting structure in terms of its external appearance. When attaching and detaching the cable, the cable can be demounted and mounted through the connector by loosening the screw fastening portion and removing the screw.

BRIEF DESCRIPTION OF THE DRAWINGS

Other objects and advantages of the present invention will become apparent during the following discussion taken in conjunction with the reference drawings, in which.

DESCRIPTION OF THE PREFERRED EMBODIMENT

Figure 1:
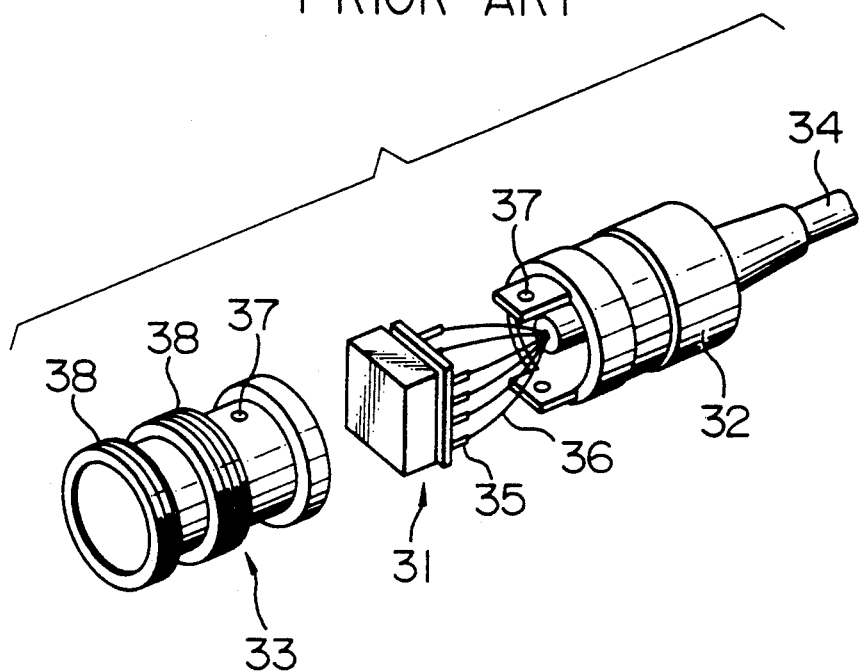
FIG. 1 is a block diagram illustrating a conventional solid state image sensing apparatus.
Figure 2:
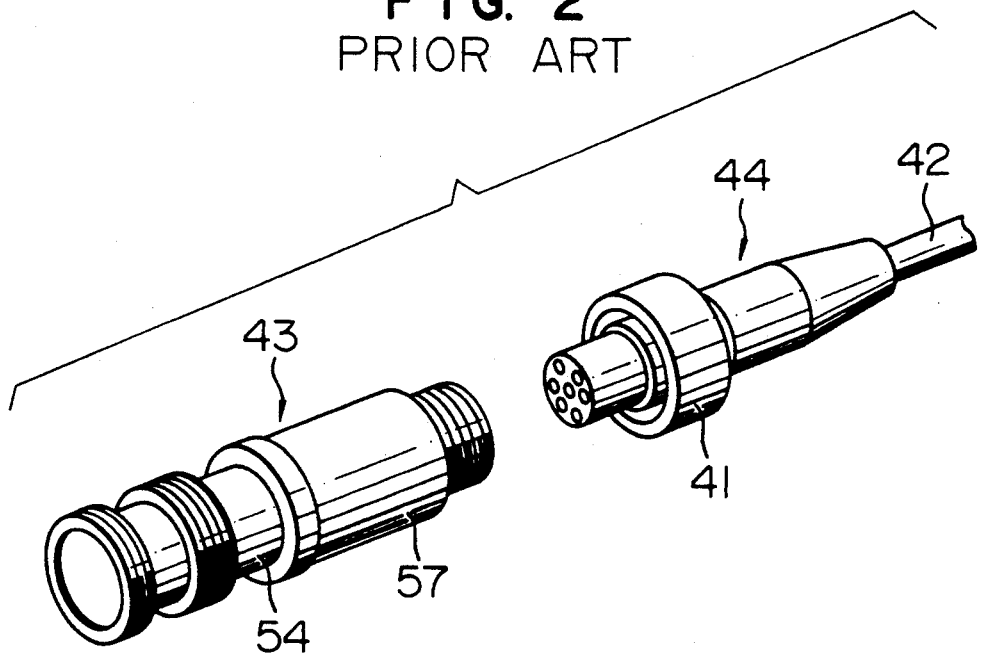
FIG. 2 is a sketch drawing of another conventional solid state image sensing apparatus.
Figure 3:
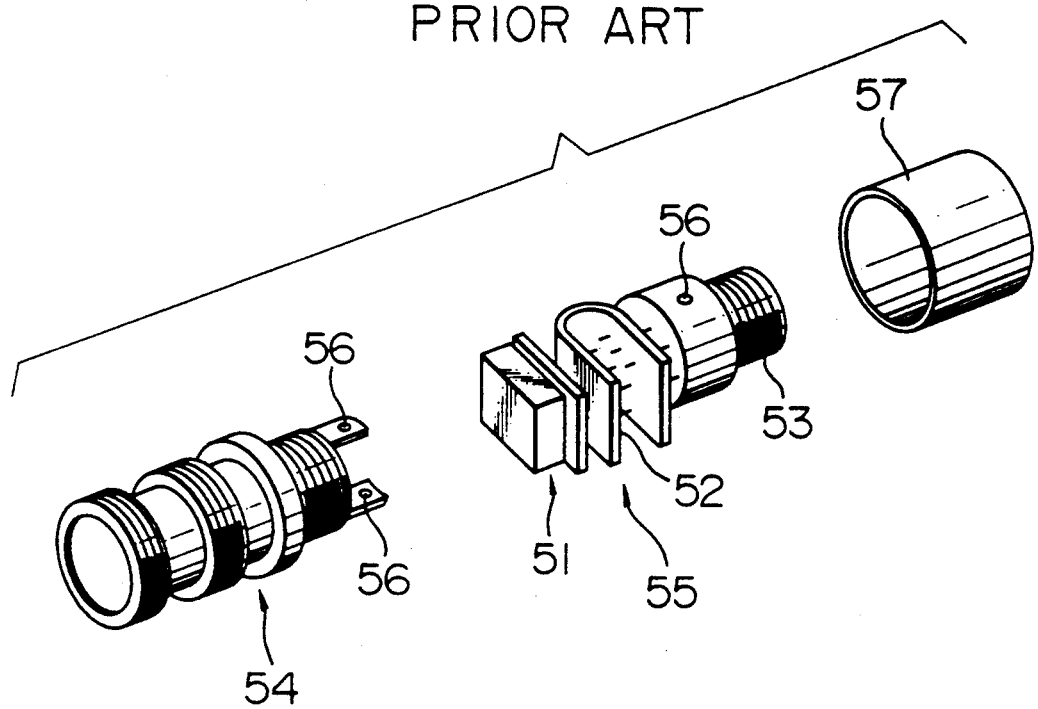
FIG. 3 is a view fully depicting a construction of the solid state image sensing apparatus of FIG. 2.
Figure 4:
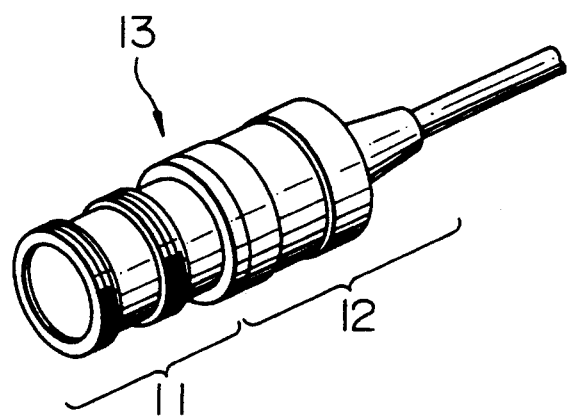
FIG. 4 is a sketch drawing of a solid state image sensing apparatus in one embodiment of the present invention.
Figure 5:
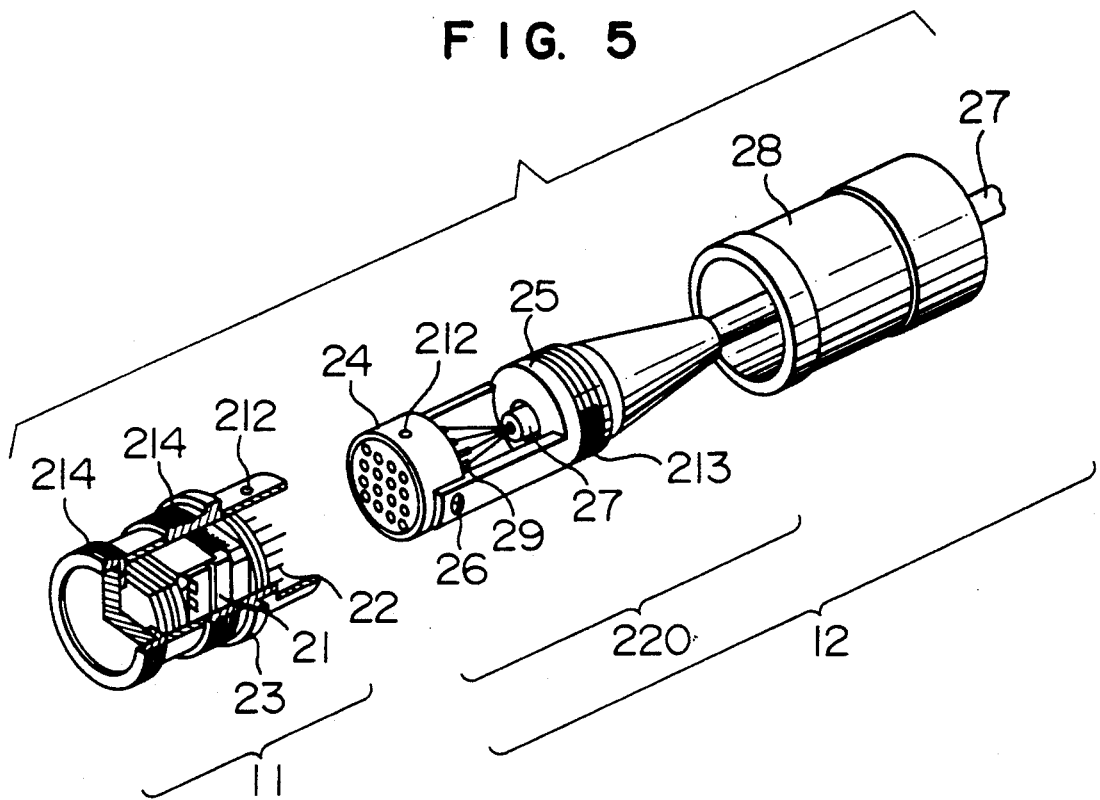
FIG. 5 is a block diagram fully illustrating the solid state image sensing apparatus shown in FIG. 4.

FIG. 4 is a sketch drawing of a solid state image sensing apparatus in one embodiment of the present invention. FIG. 5 illustrates a construction of the solid state image sensing apparatus in the embodiment. FIG.

6 depicts a construction of an image sensing module unit in the embodiment. Referring to FIGS. 4 and 5, the numeral 11 designates an image sensing device module; 12 a connector module; 13 a camera head; and 21 an image sensing device module unit consisting of lead terminals 22 incorporating a pin function of a male connector, an image sensing device chip, a device driving circuit board and a spatial filter.

Figure 6:
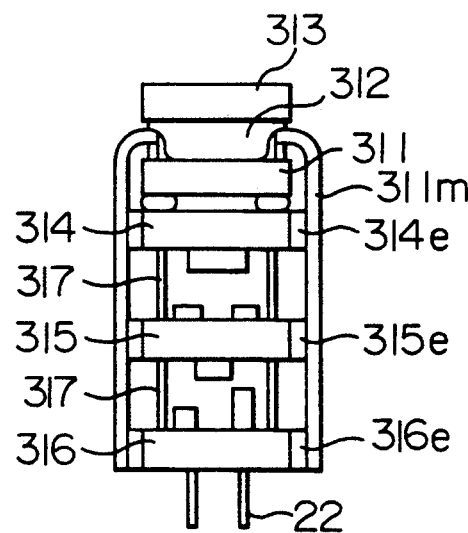
FIG. 6 is a block diagram fully illustrating an image sensing device module unit shown in FIG. 5.

Herein, the image sensing device module unit 21 is, as illustrated in FIG. 6, composed of an image sensing device chip 311, an optical glass 313, device driving circuit boards 314, 315, 316 each packed with a driving circuit for the image sensing device chip 311, and lead terminals 22. Then, the optical glass 313 is fitted to a light receiving surface of the image sensing device chip 311. The device driving circuit boards 314, 315, 316 are held and fixed with connecting pins 317. Besides, electrodes 314e, 315e, 316e are formed on the side portions of the device driving circuit boards 314, 315, 316. These electrodes are connected to an outer lead 311m connected to a device electrode (unillustrated) of the image sensing device chip 311. Further, metallic lead terminals 22 are attached to the bottom of the device driving circuit board 316.

Turning next to FIG. 5, the numeral 23 represents a sheath chassis into which the image sensing device module unit 21 is fixedly inserted. An image sensing device module 11 is thus completed. Designated at 24 is a female connector fixed to a cable clamp 25 with a screw 26. A camera cable generally indicated at 27 passes through through-holes of the body chassis 28 and the cable clamp 25 and is thereafter fixed in a predetermined position of the cable clamp 25; and terminals thereof are soldered to cable connecting terminals 29 of the female connector 24. A connector unit 220 and a connector module 12 are thus completed.

Next, lead terminal pins 22 of the image sensing device module are connector-joined to the female connector 24 of the connector module. After they have been made integral by fastening with a screw 212, the body chassis and the cable clamp are screw-fastened and united by engaging a thread (unillustrated) formed inwardly of the body chassis 28 with a thread 213 formed in an outer periphery of the cable clamp, thus completing the camera head 13. Note that a thread 214 is formed in an outer periphery of the sheath chassis 23, whereby a lens (not shown) is mountable thereto.

As discussed above, in accordance with this embodiment, the image sensing device module incorporates the image sensing device module unit in which the image sensing device chip is directly connected to the sheath chassis. The image sensing device module is connected to the connector module in which the body chassis incorporates the connector unit, thus completing the camera head. The camera head therefore takes a cable direct fitting structure in terms of its external appearance. Provided further is the connector structure in which the cable is attachable and detachable simply by demounting the screw fastening portion of the connecting member. Hence, it is possible to provide the camera head structure which sufficiently satisfies the demand of the customer.

Although the illustrative embodiment has been described in detail with reference to the accompanying drawings, it is to be understood that the present invention is not limited to this embodiment. Various changes or modification may be effected therein by one skilled in the art without departing from the scope or spirit of the invention.

What is claimed is:

1. A separable type camera head comprising:
 a cable clamp and a body chassis each having a through-hole;
 a female connector fixed to said cable clamp;
 a cable connected to cable-connecting terminals of said female connector via said through-holes of said body chassis and said cable clamp;
 an image sensing device module including: (i) an image sensing device chip having an electrode, (ii) a metallic lead, (iii) device driving boards, said electrode being connected through said metallic lead to electrodes disposed on side surfaces of said device driving circuit boards, and (iv) lead terminals disposed on said device driving circuit board, a signal of said image sensing device chip being transmitted to said cable when said lead terminals are inserted into said female connector;
 a sheath chassis encasing said image sensing device module; and
 means for fastening said sheath chassis and said female connector together, said body chassis including a first screw thread formed inwardly of said body chassis and said cable clamp having a second screw thread formed in an outer periphery of said cable clamp, said body chassis and said cable clamp being fastened to one another via screwable engagement of said first and second threads to cause said body chassis to be united with said sheath chassis.

* * * * *